(12) United States Patent
Farley

(10) Patent No.: US 8,702,725 B2
(45) Date of Patent: Apr. 22, 2014

(54) METHODS AND SYSTEMS FOR PEDICLE ACCESS

(75) Inventor: Daniel K. Farley, Traverse City, MI (US)

(73) Assignee: Thompson Surgical Instruments, Inc., Traverse City, MI (US)

(*) Notice: Subject to any disclaimer, the term of this patent is extended or adjusted under 35 U.S.C. 154(b) by 0 days.

(21) Appl. No.: 13/276,031

(22) Filed: Oct. 18, 2011

(65) Prior Publication Data

US 2013/0096619 A1    Apr. 18, 2013

(51) Int. Cl.
*A61B 19/00* (2006.01)
(52) U.S. Cl.
USPC .......................................... 606/130
(58) Field of Classification Search
USPC ....... 606/86 R, 130; 269/45, 71, 75; 294/100, 294/115; 81/487
See application file for complete search history.

(56) References Cited

U.S. PATENT DOCUMENTS

| 4,949,707 A * | 8/1990 | LeVahn et al. ............... 600/234 |
| 5,380,338 A * | 1/1995 | Christian ..................... 606/130 |
| 2004/0193018 A1 * | 9/2004 | Thalgott et al. ............ 600/227 |
| 2009/0204074 A1 * | 8/2009 | Powers et al. ............... 604/131 |

* cited by examiner

*Primary Examiner* — Christian Sevilla
(74) *Attorney, Agent, or Firm* — McAndrews, Held & Malloy, Ltd.

(57) ABSTRACT

A method of positioning a device for pedicle access includes securing a clip in an adjustable frame assembly and securing the device in the clip. The method also includes positioning the device at an initial position having a trajectory estimated to allow the device to penetrate a pedicle without damaging the nervous system, and determining whether the trajectory of the initial position is proper to avoid damage. Further, the method includes re-positioning the device to a new position if the trajectory of the initial position is not proper to avoid damage to the nervous system, and determining whether the trajectory of the new position is proper to avoid damage. The method also includes repeating the steps of re-positioning the device and determining whether the trajectory of the new position is proper as required until a proper trajectory is obtained.

6 Claims, 5 Drawing Sheets

METHODS AND SYSTEMS FOR PEDICLE ACCESS

CROSS-REFERENCE TO RELATED APPLICATION

None.

STATEMENT REGARDING FEDERALLY SPONSORED RESEARCH OR DEVELOPMENT

None.

BACKGROUND OF THE INVENTION

The present invention relates to systems and methods for providing access to pedicles during spinal procedures, for example spinal fusion.

Spinal fusion is a surgical procedure that fuses two or more vertebrae together using bone graft materials supplemented with devices. Spinal fusion may be performed for the treatment of chronic neck and/or back pain, trauma, and neoplasms. Spinal fusion can be used to stabilize and eliminate motion of vertebrae segments that may be unstable, or move in an abnormal way, that can lead to discomfort and pain. Spinal fusion may be performed to treat injuries to the vertebrae, degeneration of spinal discs, abnormal spinal curvature, and/or a weak or unstable spine.

Spinal fusion generally requires a graft material, usually bone material, to fuse the vertebrae together. The bone graft material can be placed over the spine to fuse adjacent vertebrae together. Alternatively, a device may be positioned between the vertebrae being fused and filled with the bone graft material. Such a device can include holes that allow the vertebrae and the graft material to grow together to provide fusion, with the cage supporting the weight of the vertebrae while the fusion is occurring. Because the fusion mass is under pressure, fusion can be promoted. The disc space height can be restored, taking pressure off of the nerves. The spine alignment, for aminal height, and canal diameter can be restored. In some cases the graft can be placed with minimal disruption of muscles and ligaments using minimally invasive approaches to the spine, thus preserving the natural anatomical integrity of the spine. Other interbody device assemblies are also presently known.

Rods may be used to immobilize the vertebrae being fused to allow for improved fusion. Such rods may be mounted to the vertebrae using pedicle screws. The pedicle screws are threaded through the pedicles and into the vertebral bodies. Because of the proximity of the spinal cord as well as additional nerve bodies, such screws must be placed accurately to avoid injury to the nervous system.

To help position devices, such as K-wires, that can be used to orient dilators and pedicle screws being inserted into and/or toward the vertebrae, a hollow needle may be used. For example, with a hollow needle positioned with its distal end abutting or penetrating a pedicle, a K-wire may be inserted into the pedicle, and the needle removed. Dilators may then be used to increase the area of access. The K-wire may then be removed and the pedicle screw installed.

However, the trajectory of the needle must be properly aligned to avoid driving the K-wire, dilators, or pedicle screw into the spinal column or other nerve bodies. X-rays may be used to check the trajectory of the needle. If the trajectory is not acceptable, the needle may be re-oriented and another x-ray taken. Because the trajectory may be difficult to correctly align, a large number of re-orientations and x-rays may be required, such as, for example, 20 x-rays. Holding the needle in place manually exposes the practitioner to repeated radiation. The needle may be provided with a handle, for example, to attempt to help keep the practitioner's hand out of a radiation field. However, due to the distance of the handle from the edge of the needle as well as the inherent instability of manually holding the handle and needle, the trajectory may not remain constant, resulting in the ending trajectory differing from the trajectory at the time of the x-ray.

Various frames, arms, and clamps are known for use with, for example, positioning endoscopes. These devices, however, are not well suited for manipulating the above described devices due, for example, to their size, bulkiness, and interference with an x-ray field.

It is therefore one object of the present invention to provide systems and methods that provide for improved manipulation and positioning of needles or other devices used to access pedicles during spinal procedures.

BRIEF SUMMARY OF THE INVENTION

These and other objects of the invention are achieved in a method of positioning a device for pedicle access. In certain embodiments, the method includes securing a clip in an adjustable frame assembly and securing the device in the clip. The method also includes positioning the device at an initial position having a trajectory estimated to allow the device to penetrate a pedicle without damaging the nervous system, and determining whether the trajectory of the initial position is proper to avoid damage. Further, the method includes re-positioning the device to a new position if the trajectory of the initial position is not proper to avoid damage to the nervous system, and determining whether the trajectory of the new position is proper to avoid damage. The steps of re-positioning the device and determining whether the trajectory of the new position is proper may be repeated as required until a proper trajectory is obtained.

In certain embodiments, determining whether the trajectory of the initial position and/or the new position is proper includes taking an x-ray image of anatomy proximate to the device and position being determined and analyzing the x-ray.

In certain embodiments, securing the device for pedicle access in the clip includes advancing a sleeve of the clip forward to move jaws of the clip from an open position toward a closed position. For example, in certain embodiments the sleeve is threaded and the jaws include sloped surfaces. Also, advancing the sleeve may include rotating the sleeve with respect to a shaft with which the sleeve is in threaded engagement, such that the sloped surfaces of the jaws are acted upon by the sleeve to move the jaws toward the closed position.

Further, in certain embodiments, the clip includes a plurality of differently sized openings for accepting different sizes of devices, and securing the device for pedicle access in the clip includes selecting an appropriate one of the plurality of differently sized openings into which to place the device for pedicle access, based on the size of the device.

Certain embodiments of the present invention provide a method of positioning a device for pedicle access utilizing a frame and a clip. For example, in certain embodiments, the frame includes a plurality of arms joined by joints that are configured to allow the arms to be adjustable with respect to each other, and the clip includes jaws configured to grasp the device for pedicle access. Also, the clip is configured to be securable to the frame. The method includes securing the clip in the frame and securing the device for pedicle access in the jaws of the clip. The method also includes manipulating the arms of the frame to position the device at an initial position having a trajectory estimated to allow the device to penetrate a pedicle without damaging a patient's nervous system, wherein, the frame maintains the device in the initial position, and taking an image for determining whether the trajectory of the initial position is proper to avoid damage to the nervous system. Further, the method includes re-positioning the device to a new position by manipulating the arms if the trajectory of the initial position is not proper to avoid damage to the nervous system, and taking an image for determining whether the trajectory of the new position is proper to avoid damage to the nervous system. The method also includes repeating the steps of re-positioning the device and taking an image for determining whether the trajectory of the new position is proper as required until a proper trajectory is obtained.

Additionally, in certain embodiments, securing the device for pedicle access in the jaws of the clip includes advancing a sleeve of the clip to urge the jaws together. For example, the sleeve may be threaded, and the jaws may include sloped surfaces. Advancing the sleeve may include rotating the sleeve with respect to a shaft with which the sleeve is in threaded engagement. The jaws extend substantially parallel to the shaft with which the sleeve is in threaded engagement, and the sloped surfaces of the jaws are acted upon by the sleeve to move the jaws toward the closed position.

Further, in certain embodiments, the jaws of the clip include notches that cooperate to define a plurality of differently sized openings for accepting different sizes of devices. Securing the device for pedicle access in the jaws of the clip includes selecting an appropriate one of the plurality of differently sized openings into which to place the device for pedicle access.

Certain embodiments of the present invention provide a system for positioning a device for pedicle access. The system includes a clip for securing the device for pedicle access, and a frame for securing the clip. The clip is constructed of a radiolucent material and includes jaws and a shaft. The jaws extend substantially parallel from the shaft and are biasable from an open position to a closed position. The jaws accept the device for pedicle access in the open position and secure the device for pedicle access in the closed position. In certain embodiments, the jaws may include a plurality of notches that cooperate to form a plurality of differently sized openings. Differently sized devices may be secured in the clip by selecting an appropriate one of the openings into which to insert the device. The frame includes a plurality of arms joined by joints. The joints are configured to allow the arms to be adjustable with respect to one another when the arms are manipulated by a sufficient outside force and to maintain the arms in position when the arms are not subjected to a sufficient outside force.

DETAILED DESCRIPTION

Figure 1:
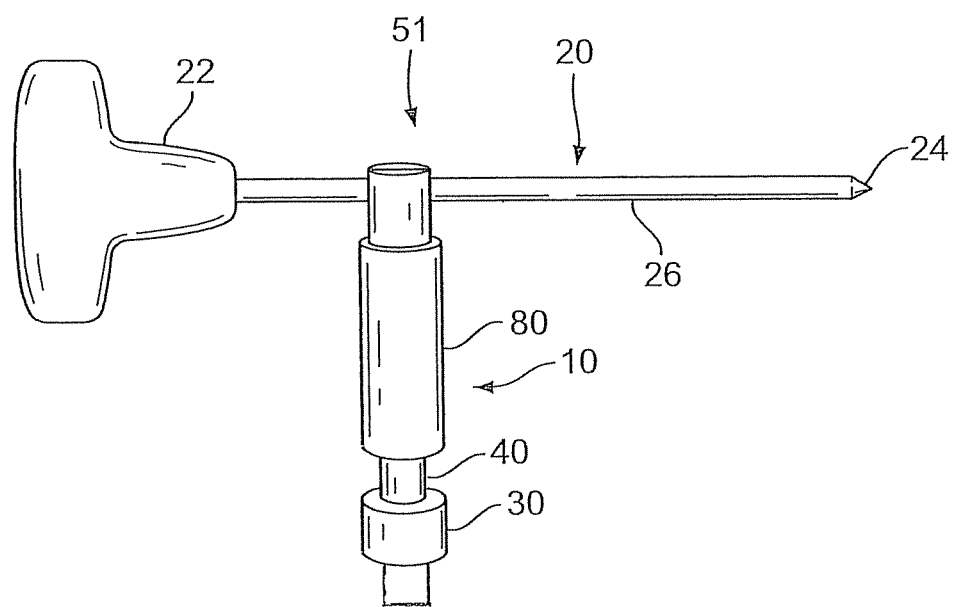
FIG. 1 illustrates a perspective view of a clip assembly formed in accordance with an embodiment of the present invention.
Figure 2:
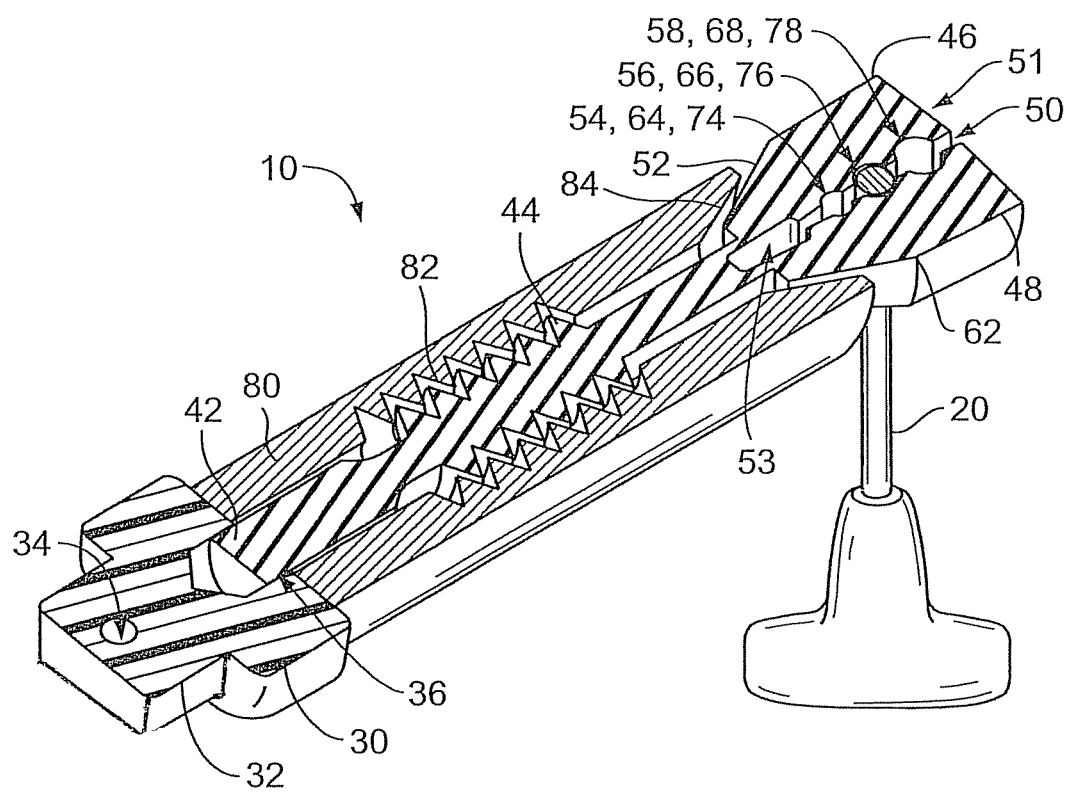
FIG. 2 illustrates a sectional view through the clip assembly of FIG. 1 with the clip assembly in an open position.
Figure 3:
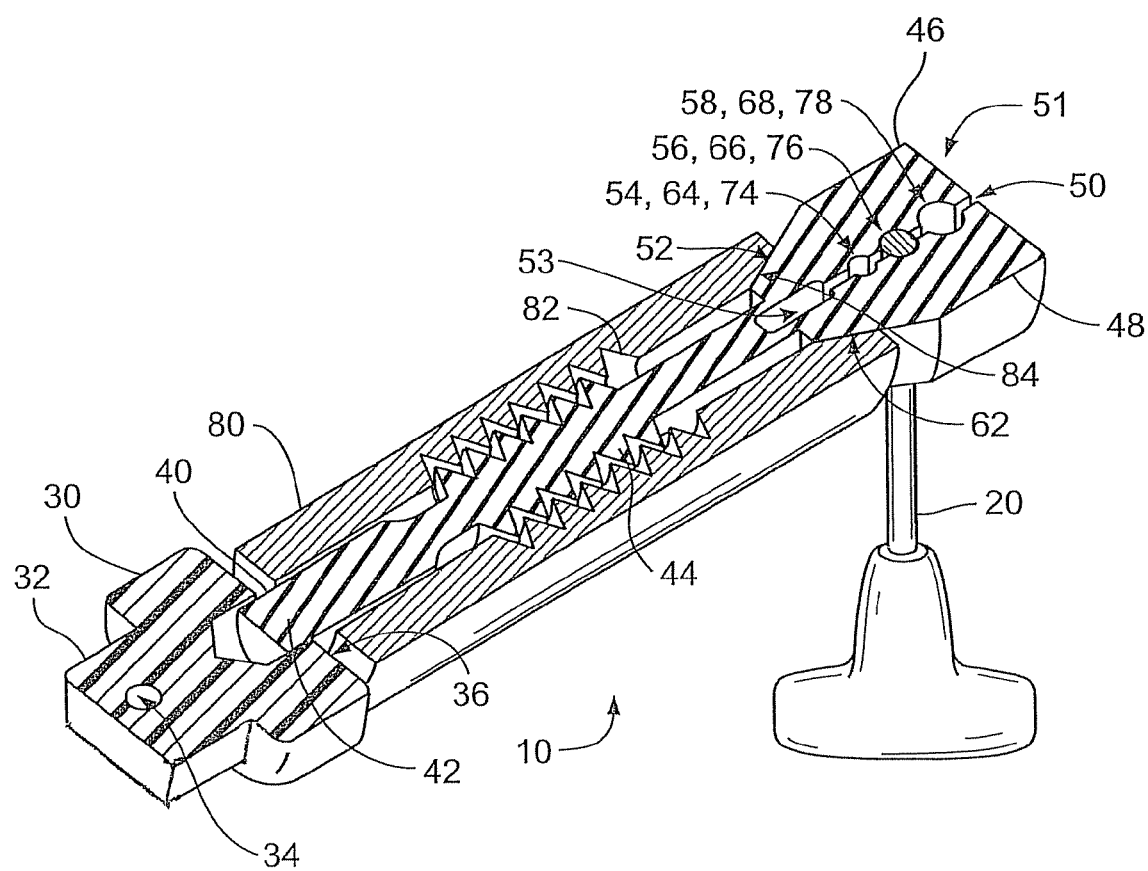
FIG. 3 illustrates a sectional view through the clip assembly of FIG. 1 with the clip assembly in a closed position.

FIG. 1 illustrates a perspective view of a clip assembly 10 configured and adapted to secure a pedicle needle 20 in place during a spinal procedure. FIG. 2 illustrates a sectional view through the clip assembly 10 with the clip assembly in an open position, and FIG. 3 illustrates a sectional view through the clip assembly 10 with the clip assembly 10 in a closed position. As seen in FIG. 1, in the illustrated embodiment, the pedicle needle 20 includes a handle 22 positioned proximally and a tip 24 positioned distally and configured to abut and/or penetrate a pedicle. The pedicle needle 20 also includes a barrel 26 that extends through the pedicle needle 20. The barrel 26 is hollow and designed to accept and position a K-wire to be driven into the pedicle of a patient.

As seen in FIGS. 2-3, the clip assembly 10 includes a mounting portion 30, a shaft 40, and a sleeve 80. The mounting portion 30 accepts the shaft 40 and is configured to facilitate mounting, for example, to a clamp and/or an arm of a mounting system. The shaft 40 is an example of a grasping member, and is configured to grasp and secure a pedicle device such as the pedicle needle 20. The sleeve 80 cooperates with the shaft 40 to move the shaft 40 between closed and open positions to grasp or release a pedicle device as appropriate. The clip assembly 10 may be constructed, for example, of a surgical grade sterilizeable plastic that is x-ray transparent, or radiolucent. This helps to minimize any interference that may be caused by the clip assembly 10 while taking images to determine the position of a pedicle device.

In the illustrated embodiment, the mounting portion 30 includes a tab 32, a mounting hole 34, and a bore 36. The tab 32 includes flattened surfaces for ease of handling as well as for mating with a slot of a mounting system. Further, the mounting hole 34, positioned proximate to the tab 32, is designed to accept a pin for securing the mounting portion to a mounting system. Other mounting features or configurations may be used.

The bore 36 of the mounting portion 30 is configured to accept an end of the shaft 40 for mounting the shaft 40 to the mounting portion 30. The shaft 40 may be mounted in the bore 36 by a variety of means, such as an interference fit, a pin or pins, or a set screw. Other mounting configurations may be employed. Further, in certain embodiments, the mounting portion and shaft may be formed as a single piece.

The shaft 40 of the illustrated embodiment includes a first end 42, a threaded portion 44, a first jaw 46, and a second jaw 48. The first and second jaws 46, 48 are separated by a gap 50 and are configured to be biasable toward each other. The first jaw 46, second jaw 48, and gap 50 cooperate to help form a gripping portion 51 adapted to grasp a pedicle device, such as pedicle needle 20. The shaft 40 of the illustrated embodiment has a generally circular cross-section.

The first end 42 of the illustrated embodiment is generally cylindrically shaped and configured to be mounted in the bore 36 of the mounting portion 30. The threaded portion 44 of the shaft 40 is positioned intermediately between the first end 42 and the first and second jaws 46, 48. The threaded portion 44 is configured to cooperate with a corresponding threaded portion of the sleeve 80 to provide for linear translation of the sleeve 80 relative to the shaft 40.

The first jaw 46, as illustrated in FIGS. 2-3, includes a sloped surface 52 that slopes outwardly from a central axis of the shaft 40. The exterior of the sloped surface 52 is generally round across its width, and the sloped surface 52 is sized and configured to cooperate with a corresponding sloped surface on the sleeve 80. The first jaw 46 also includes a first notch 54, a second notch 56, and a third notch 58. These notches cooperate with corresponding notches in the second jaw 48 to form openings for grasping pedicle devices such as pedicle needles. The notches are of different sizes to allow for grasping of differently sized devices.

Similarly, the second jaw 48, as illustrated in FIGS. 2-3, includes a sloped surface 62 that slopes outwardly from a central axis of the shaft 40. The exterior of the sloped surface 62 is generally round across its width, and the sloped surface 62 is sized and configured to cooperate with a corresponding sloped surface on the sleeve 80. The second jaw 48 also includes a first notch 64, a second notch 66, and a third notch 68. These notches, as indicated above, cooperate with corresponding notches in the first jaw 46 to form openings for grasping pedicle devices such as pedicle needles. The notches are of different sizes to allow for grasping of differently sized devices. For example, in the illustrated embodiments, first notches 54 and 64 cooperate to form a first opening 74 sized to accept a first range of diameters, second notches 56 and 66 cooperate to form a second opening 76 sized to accept a second range of diameters, and third notches 58 and 68 cooperate to form a third opening 78 sized to accept a third range of diameters. The third range of diameters is generally larger than the second range of diameters, which is generally larger than the first range of diameters. In the illustrated embodiment, the jaws include three sets of notches forming three openings. Other numbers of notches and openings may be employed in other embodiments. For example, in certain embodiments, only one opening may be provided. The openings are generally shaped as semi-circles separated by the gap 50. When the first and second jaws 46, 48 are urged together, the size of the gap 50 and openings reduce so that they may grasp a desired object. When the first and second jaws 46, 48 are not subject to any force urging them together, the openings are large enough to allow the object to be placed into the desired opening or removed from the appropriate opening.

The gap 50 (along with the notches) is sized to allow the openings to have adequate clearance between the jaws to grasp and release a desired size range of pedicle devices. The gap 50 is reduced in size (along with the size of the openings) when the two jaws are urged together by an external force. In the illustrated embodiments, the gap 50 includes an enlarged relief area 53 to reduce the force required to urge the jaws together.

In the illustrated embodiment, the jaws may be urged together through the use of the sleeve 80. The sleeve 80 is generally cylindrical in shape, and has a generally cylindrical bore extending through its length. The sleeve 80 is sized to accept the shaft 40. The sleeve 80 includes a threaded portion 82 and a tapered surface 84. The threaded portion 82 is configured to cooperate with the threaded portion 44 of the shaft 40 to provide linear translation of the sleeve 80 relative to the shaft 40 when the sleeve 80 is rotated with respect to the shaft 40. Rotation in one direction advances the sleeve 80 toward the jaws, and rotation in the opposite direction advances the sleeve toward the first end 42.

The tapered surface 84 of the sleeve 80 is sized and configured to cooperate with the sloped surfaces 52, 62 of the first and second jaws 46, 48. When the sleeve 80 is urged toward the jaws (by rotation in the illustrated embodiment), the tapered surface 84 is brought into contact with the sloped surfaces 52, 62. Further urging of the sleeve 80 toward the jaws results in the tapered surface 84 pressing against the sloped surfaces 52, 62 and thereby urging the jaws together.

Thus, by rotating the sleeve 80 in a first direction, the jaws may be brought together to grasp a pedicle device. Rotating the sleeve 80 in the opposite direction urges the sleeve toward the first end 42 of the shaft 40, removing the contact between the tapered surface 84 and the sloped surfaces 52, 62, thereby removing the force urging the jaws together and allowing the jaws to return to the open position.

The clip assembly 10 may be assembled by first sliding the shaft 40 into the sleeve 80 and engaging the threaded portions of the shaft 40 and sleeve 80 to mount the sleeve 80 on the shaft 40. Then, the first end 42 of the shaft 40 may be mounted in the bore 36 of the mounting portion 30. To secure a pedicle device in the clip assembly 10, the clip assembly 10 is started in the open position (see FIG. 2), that is, with sleeve 80 positioned toward the first end 42 such that the tapered surface 84 is not urging the jaws 46, 48 of the shaft 40 together. Based on the size of the portion of the pedicle device to be secured, the appropriate opposing notches are selected, and the portion of the pedicle device to be secured is slid through the gap 50 to the appropriate opposing notches. Then, the clip assembly 10 is moved to a closed position by rotating the sleeve 80 to translate it toward the jaws of the shaft 40, thereby urging the jaws closed, reducing the size of the opening, and securing the portion of the pedicle device in the opening. In the illustrated embodiment, a portion of the shaft of a hollow pedicle needle 20 is grasped.

In the illustrated embodiment, the shaft, threads, and other components of the clip assembly are configured so that the jaws extend generally parallel to an axis defined by the shaft. In other embodiments, other arrangements may be employed. For example, in certain embodiments, the jaws may be formed as separate pieces from the shaft, and, further, may extend generally perpendicularly to an axis defined by the shaft.

Figure 4:
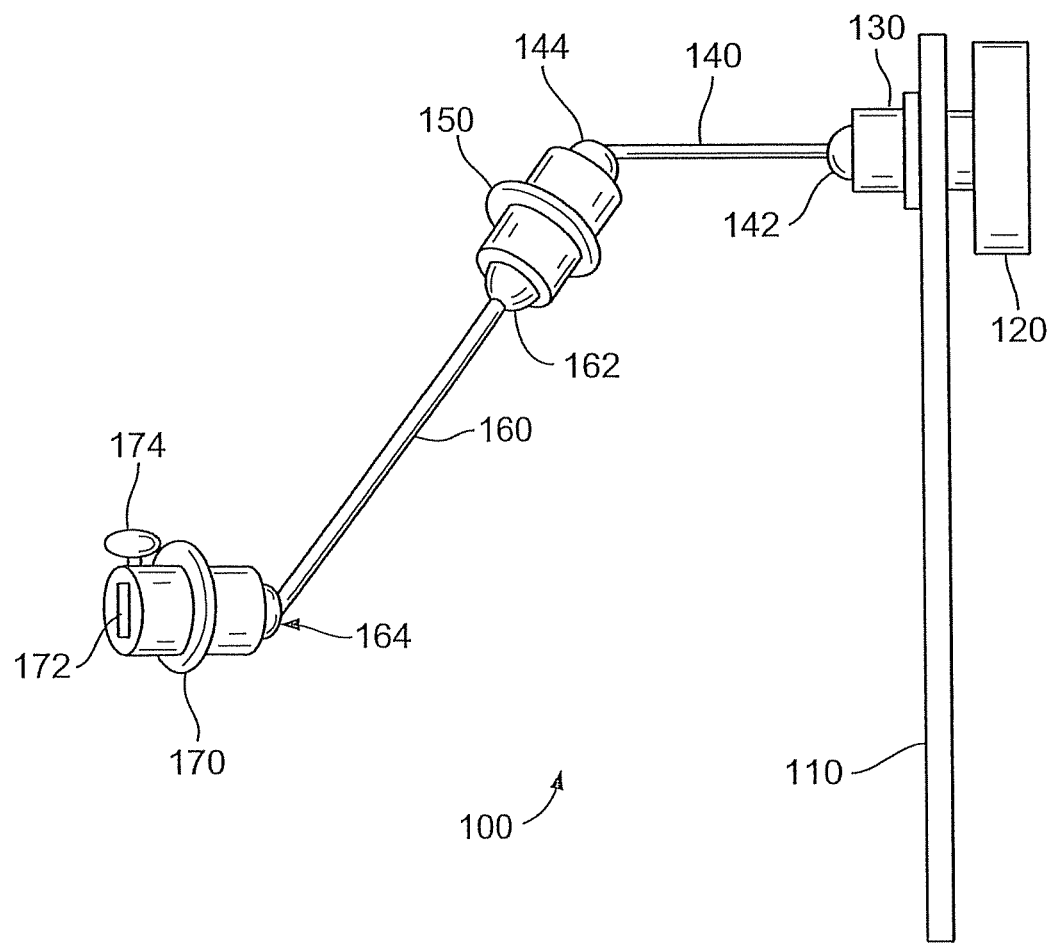
FIG. 4 illustrates a perspective view of a frame system formed in accordance with an embodiment of the present invention.

To manipulate and position the clip assembly 10 and pedicle needle 20, a frame system may be used. FIG. 4 illustrates a perspective view of a frame system 100 formed in accordance with an embodiment of the present invention. The illustrated frame system 100 includes a rail arm 110, a rail joint 120, a shoulder joint 130, a first arm 140, a second joint 150, a second arm 160, and an end joint 170.

The rail arm 110 is a generally straight arm adapted to be mounted to, for example, the rail of a hospital bed. The rail arm 100 is joined to the first arm 140 via a shoulder joint 130 and a rail joint 120. The rail joint 120 may be, for example, a universal joint. In the illustrated embodiment, the shoulder joint 130 accepts a first ball end 142 of the first arm 140 in a ball and socket arrangement, allowing the first arm to be oriented in a wide variety of positions relative to the rail arm 100. In the illustrated embodiment, the shoulder joint 130 is set with a pre-set tension (for example, as part of an assembly including a spring compressed a given amount) that allows the ball to rotate within the joint when subject to a sufficient outside force (such as a practitioner manipulating the first arm), but still provides adequate stability to maintain the first arm 140 in place when not subject to such a sufficient outside force. Thus, the frame may be adjustable by hand but remain rigidly in position when released by hand. Further, this tension may be adjustable to increase or decrease the tension in the joint as appropriate.

The first arm 140 terminates in a second ball end 144 that is accepted by the second joint 150. The second joint 150 also accepts a first ball end 162 of the second arm 160. In the illustrated embodiment, each of these ball ends are configured and mounted similarly to the above described mounting of the shoulder joint 130, thereby allowing for a wide range of motion and possible orientations between the first arm 140 and the second arm 160. In alternate embodiments, other types and/or numbers of joints or arms may be used. For example, hinged joints may be used, or an arm that articulates at an increased number of joints may be employed.

The second arm 160 terminates in a second ball end 164 that is accepted by the end joint 170 in a similar fashion as described above, allowing for a wide range of manipulation of the end joint 170 relative to the second arm 160. The end joint 170 also includes a slot 172 and a knob 174. The slot 172 is sized and configured to accept the tab 32 of the mounting portion 30 of the clip assembly 10. In the illustrated embodiment, the knob 174 is knurled to provide a convenient grip, and is used to actuate a pin (not shown) that cooperates with the mounting hole 34 for securing or releasing the mounting portion 30 from the slot 172.

Figure 5:
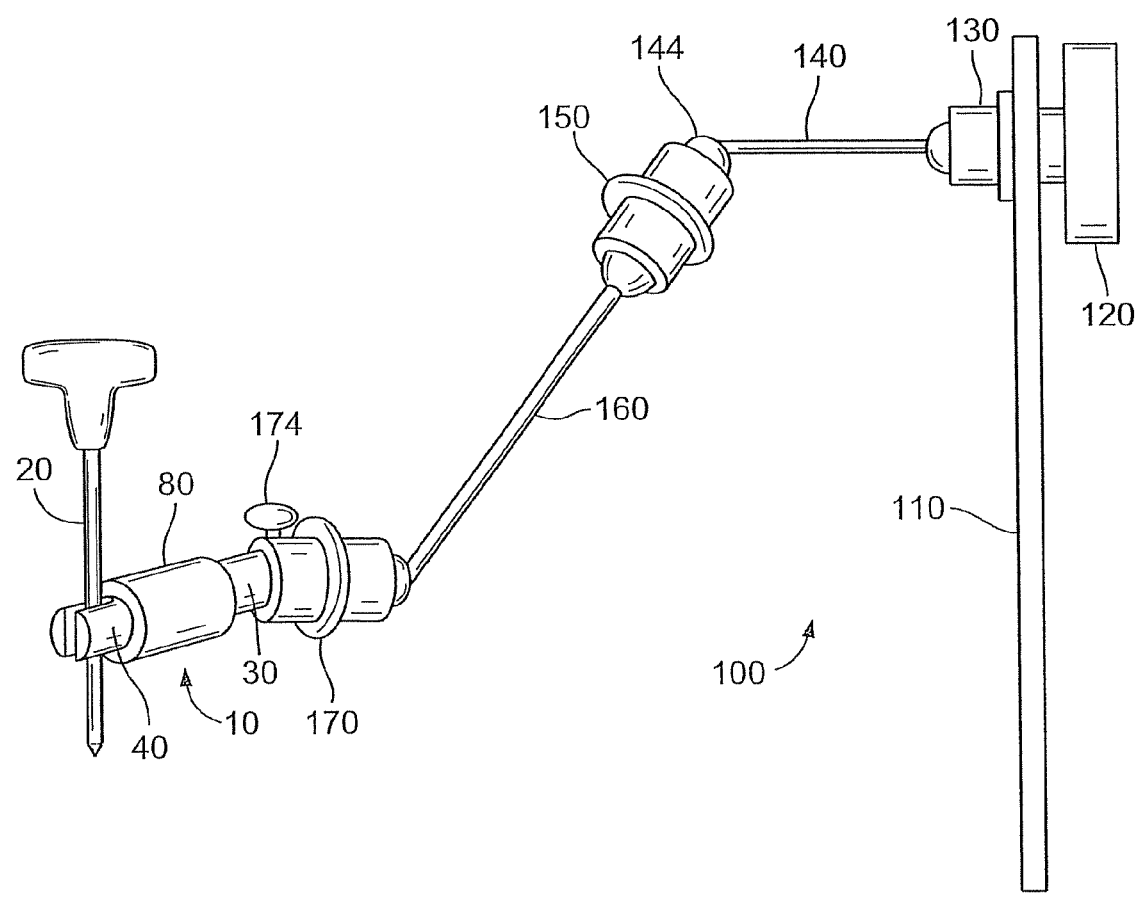
FIG. 5 illustrates a perspective view of a clip assembly in use with a frame system to position a pedicle needle in accordance with an embodiment of the present invention.

FIG. 5 illustrates a perspective view of a clip assembly 10 in use with a frame system 100 to position a pedicle needle 20 in accordance with an embodiment of the present invention. To use the frame system 100 and clip assembly 10, the frame system 100 is secured to a rail associated with a hospital bed. Because imaging equipment will be used, the frame system 100 should be positioned so as not to interfere with the imaging equipment. The shoulder joint 130 may then be positioned as desired (for example, with the first arm 140 in a generally level position at an elevation above the site of interest and pointing generally toward the site of interest) and secured via the rail joint 120. Next, the second arm 160 may be positioned. A proper range of motion can generally be achieved by having the second arm 160 start at about a 90 degree angle to the first arm 140, with the second arm 160 pointing generally toward the site of interest.

With the frame system 100 positioned as described above, the patient and frame system 100 may be draped with sterile drape as appropriate. Next, the tab 32 of the clip assembly 10 may be inserted into the slot 172 of the end joint 170 and the clip assembly 10 secured to the frame system 100. The pedicle needle 20 is then positioned at approximately the target site. With the clip assembly 10 in the open position, the clip assembly 10 is then brought toward the pedicle needle 20. The gap 50 of the clip assembly is then slid over the portion of the pedicle needle 20 intended to be secured until the pedicle needle 20 is within the opposing notches forming the desired opening based on the size of the pedicle needle 20. With the pedicle needle 20 thus positioned in the desired opening, the sleeve 80 is then rotated to advance the sleeve 80 laterally along the shaft 40 toward the jaws. As the tapered surface 84 of the sleeve 80 contacts the sloped surfaces of the jaws and is further advanced, the jaws are urged together to grasp the pedicle needle 20. The sleeve 80 should be advanced such that the clip assembly 10 can hold the pedicle needle 20 without slippage or sliding, but not so tightly as to damage the pedicle needle 20. Selection of the proper opening for use with a given needle size will also help to provide a secure grip and/or prevent damage.

The pedicle needle 20 is then positioned, by hand, at an initial position. The initial position is selected so that the estimated trajectory of the pedicle needle 20 is oriented into the pedicle, and such that the pedicle needle 20 is estimated to not damage the spinal cord or other portions of the nervous system along the trajectory into the pedicle and vertebral body. This positioning can be achieved in the soft tissue with the tip of the pedicle needle proximate to the pedicle. The frame system 100 and clip assembly 10 hold the pedicle needle 20 in place at the initial position, allowing the practitioner's hands to be released from the pedicle needle 20 and frame system 100 while an image, for example an x-ray, is taken of the area including the pedicle and pedicle needle 20.

This allows for improved stability and reduced risk of movement compared to manual holding of a pedicle device in place, as well as allowing a practitioner to reduce the amount of radiation exposure.

With the practitioner's hands free and the pedicle needle 20 maintained in position by the frame system 100, an image, such as an x-ray may be taken showing the projected trajectory of the pedicle needle 20 into the pedicle and vertebral body. From this image, it can be determined if the pedicle needle 20 is likely to damage portions of the nervous system or not. In many instances, the initial position will not be proper to avoid injury. Thus, based on the trajectory of the pedicle needle 20 as indicated by the image, the pedicle needle 20 and frame system 100 can be manipulated to reposition the pedicle needle 20 in a new position having a new trajectory. Again, a new image may be taken, with the practitioner's hands free, of the pedicle needle 20 and anatomy of interest with the pedicle needle 20 in the new position. As before, it is determined, based on the image, if the trajectory is proper to avoid damage to the nervous system. If the trajectory is not proper, the pedicle needle 20 is re-positioned, and another image taken to confirm the trajectory, with these steps repeated as required until a desired trajectory is obtained. Once a desired trajectory is obtained, the pedicle needle 20 may be advanced into the pedicle and vertebral body as desired. With the pedicle needle 20 placed as desired, the practitioner can continue with the desired procedure, for example, to place a pedicle screw.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A system for positioning a device for pedicle access comprising:
   a clip for securing the device for pedicle access, wherein the clip is constructed of a radiolucent material the clip being formed as an integral unit and including:
   a shaft having a threaded portion,
   a first jaw extending substantially parallel from the shaft, the first jaw including a first sloped surface that slopes outwardly from a central axis of the shaft,
   a second jaw opposed to the first jaw and extending substantially parallel from the shaft, the second jaw including a second sloped surface that slopes outwardly from the central axis of the shaft, the first and second jaws forming a gap therebetween,
   an elongated relief area extending along the central axis of the shaft between the threaded portion of the shaft and the gap,
   wherein the first and second jaws are biasable from an open position to a closed position, wherein the jaws accept the device for pedicle access in the open position and secure the device for pedicle access in the closed position;
   a sleeve having a bore, the bore having a threaded portion configured to engage the threaded portion of the shaft, the bore further having a sloped surface configured to engage the first sloped surface and second sloped surface of the first and second jaws, respectively, wherein relative rotation between the sleeve and the clip in a first direction drives the first and second jaws to the closed position, and wherein relative rotation between the sleeve and the clip in a second direction drives the first and second jaws to the open position; and a frame configured for securing the clip, the frame including a plurality of arms joined by joints, wherein the joints are configured to allow the arms to be adjustable with respect to one another when the arms are manipulated by a sufficient outside force and to maintain the arms in position when the arms are not subjected to a sufficient outside force.

2. The system of claim 1 wherein the clip includes a mounting tab, and the frame includes a slot configured to accept the mounting tab for securing the clip to the frame.

3. The system of claim 1 wherein the first and second jaws include a plurality of notches that cooperate to form a plurality of differently sized openings, wherein differently sized devices may be secured in the clip by selecting an appropriate one of the openings into which to insert the device.

4. A system for positioning a pedicle device at a trajectory with respect to a pedicle of a patient, the system comprising:
- a frame system having a proximal portion securable at a fixed relationship with respect to the patient, the frame system further having a distal portion that is configured for multi-axis articulation with respect to the proximal portion, wherein the distal portion is further securable at a given position after multi-axis articulation of the proximal portion; and
- a clip having a mounting portion configured for mounting proximate the distal portion of the frame system, the clip being formed as an integral unit and including:
  - a shaft having a threaded portion,
  - a first jaw extending substantially parallel from the shaft, the first jaw including a first sloped surface that slopes outwardly from a central axis of the shaft,
  - a second jaw opposed to the first jaw and extending substantially parallel from the shaft, the second jaw including a second sloped surface that slopes outwardly from the central axis of the shaft, wherein the first and second jaws define a gap therebetween,
  - an elongated relief area extending between the threaded portion of the shaft and the gap,
  - wherein the first and second jaws are biasable from an open position to a closed position, wherein the jaws accept the device for pedicle access in the open position and secure the device for pedicle access in the closed position;
- a sleeve having a bore, the bore having a threaded portion configured to engage the threaded portion of the shaft, the bore further having a sloped surface configured to engage the first sloped surface and second sloped surface of the first and second jaws, respectively, wherein relative rotation between the sleeve and the clip in a first direction drives the first and second jaws to the closed position, and wherein relative rotation between the sleeve and the clip in a second direction drives the first and second jaws to the open position; and
- wherein the frame system and clip are operable with respect to one another to sequentially position the pedicle device at multiple trajectories with respect to the patient.

5. The system of claim 4, wherein at least a portion of the clip comprises a radiolucent material.

6. The system of claim 4, wherein the frame comprises a plurality of arms joined by joints, wherein the joints are configured to allow the arms to be adjustable with respect to one another when the arms are manipulated by a sufficient outside force and to maintain the arms in position when the arms are not subjected to a sufficient outside force.

* * * * *